(12) United States Patent
Makowski et al.

(10) Patent No.: US 6,897,028 B1
(45) Date of Patent: May 24, 2005

(54) IDENTIFICATION OF MOLECULAR TARGETS

(75) Inventors: Lee Makowski, Arlington, VA (US); Diane R. Makowski, Arlington, VA (US); Hitesh J. Sanganee, Tallahassee, FL (US)

(73) Assignee: Florida State University, Tallahassee, FL (US)

( * ) Notice: Subject to any disclaimer, the term of this patent is extended or adjusted under 35 U.S.C. 154(b) by 872 days.

(21) Appl. No.: 09/110,994

(22) Filed: Jul. 7, 1998

Related U.S. Application Data

(60) Provisional application No. 60/051,780, filed on Jul. 7, 1997.

(51) Int. Cl.[7] .............................................. G01N 33/53
(52) U.S. Cl. ................................ 435/7.1; 435/6; 435/5; 435/4; 435/DIG. 15; 435/DIG. 14; 536/48; 536/49; 536/50
(58) Field of Search ............................ 435/7.1, 6, 5, 4, 435/DIG. 15, DIG. 14; 536/48–50

(56) References Cited

U.S. PATENT DOCUMENTS

| | | | |
|---|---|---|---|
| 5,133,866 A | * 7/1992 | Kauvar ........................ 210/635 |
| 5,223,409 A | 6/1993 | Ladner et al. .............. 435/69.7 |
| 5,432,018 A | 7/1995 | Dower et al. ................... 435/5 |
| 5,635,182 A | 6/1997 | McCoy et al. ........... 424/192.1 |

OTHER PUBLICATIONS

Iannolo et al, J. Mol. Biol., (1995), 248, pp 835–844.*
Yu et al, The Journ. Biol. Chem., 268(10) (Apr. 5, 1993), pp. 7520–7526.*
Luzzago, et al., Mimicking of Discontinuous Epitopes by Phage–Displayed Peptides, I. Epitope Mapping of Human H Ferritin Using a Phage Library of Constrained Peptides, Gene, vol. 128, pp. 51–57, 1993.
Miceli, et al., Two–Stage Selection of Sequences From A Random Phage Display Library Delineates Both Core Residues And Permitted Structural Range Within An Epitope, Journal of Immunological Methods, vol. 167, pp. 279–287, 1994.
Ivanekov, et al., Characterization of S–100b Binding Epitopes The Journal of Biological Chemistry, vol. 270, No. 24, pp. 14651–14658, Jun. 16, 1995.
Welply, et al., A Peptide Isolated by Phage Display Binds to ICAM–1 and Inhibits Binding to LFA–1, Proteins: Structure and Genetics, vol. 26, No. 3, pp. 262–270, 1996.
Petrenko, et al., A Library of Organic Landscapes on Filamentous Phage, Protein Engineering, vol. 9. No. 9, pp. 797–801, 1996.
Sparks, et al., Distinct Ligand Preferences of Src Homology 3 Domains from Src, Yes, Abl, Cortactin, p53bp2, PLCy, Crk, and Crb2, Proc. Natl. Acad. Sci, USA, vol. 93, pp. 1540–1544, Feb. 1996.
Hoffman, et al., Binding Properties of SH3 Peptide Ligands Identified From Phage–Displayed Random Peptide Libraries, Molecular Diversity, vol. 2 pp. 5–12, 1996.
Sparks, Cloning of Ligand Targets; Systematic Isolation of SH3 Domain–Containing Proteins, Nature Biotechnology, vol. 14, pp. 741–744, Jun. 1996.
Gies, J.P., Drug Targets—Molecular Mechanisms of Drug Action The Practice of Medicinal Chemistry (Academic Press Ltd.) pp. 56–80, 1996.
Rodi, et al., Transfer RNA Isoaceptor Availability Contributes To Sequence Censorship in a Library of Phage. Displayed Peptides, Proc. 22nd Int'l Symp., The Taniguchi Foundation, pp. 155–164, 1997.
Bremnes, et al., Selection of Phage Displayed Peptides From A Random 10–Mer Library Recongnising a Peptide Target, Immunotechnology, vol. 4, pp. 21–28, 1998.
Ph.D. Phage Display Peptide Library Kits, New England Biolabs Inc., 1998/1999 Catalog.
Cwirla, et al., Peptides on phage: A vast library of peptides For identifying ligands, Aug. 1990, vol. 87, p. 6378–6382.
Bruno, J.G., A colorimetric Inhibition Study of Single–Stranded DNA Decamer Sequence Interactions with Dinitrotoluene Biochemical and Biophysical Research Communications, 1997, vol. 236, p. 344–346.

* cited by examiner

*Primary Examiner*—T. D. Wessendorf
(74) *Attorney, Agent, or Firm*—Senniger Powers

(57) ABSTRACT

Identification of the molecular targets of a drug or toxin is the first step in understanding how the drug or toxin works, an important advance in learning how to improve a drug or assess the risks due to a toxin. The primary action of a drug usually involves binding to a protein; secondary actions may express themselves in the form of side effects and in some cases may be due to binding to other proteins. Consequently, it is useful to identify all physiologically relevant sites of action of a drug or toxin. A simple method for obtaining a list of the potential targets of a drug, toxin or other biologically active substance (referred to collectively as ligands) involves a multistep process. The first step is screening a protein or peptide library to identify library members that exhibit high affinity for a particular ligand. The second step involves searching of sequence data bases for proteins that contain the sequences of the library members shown to have high affinity for the ligand. The proteins thus identified constitute a list of potential targets for the ligand. If random peptide libraries have been used, the position of identified consensus sequences within the identified protein constitutes an identification of the potential ligand binding site on the target.

7 Claims, 6 Drawing Sheets

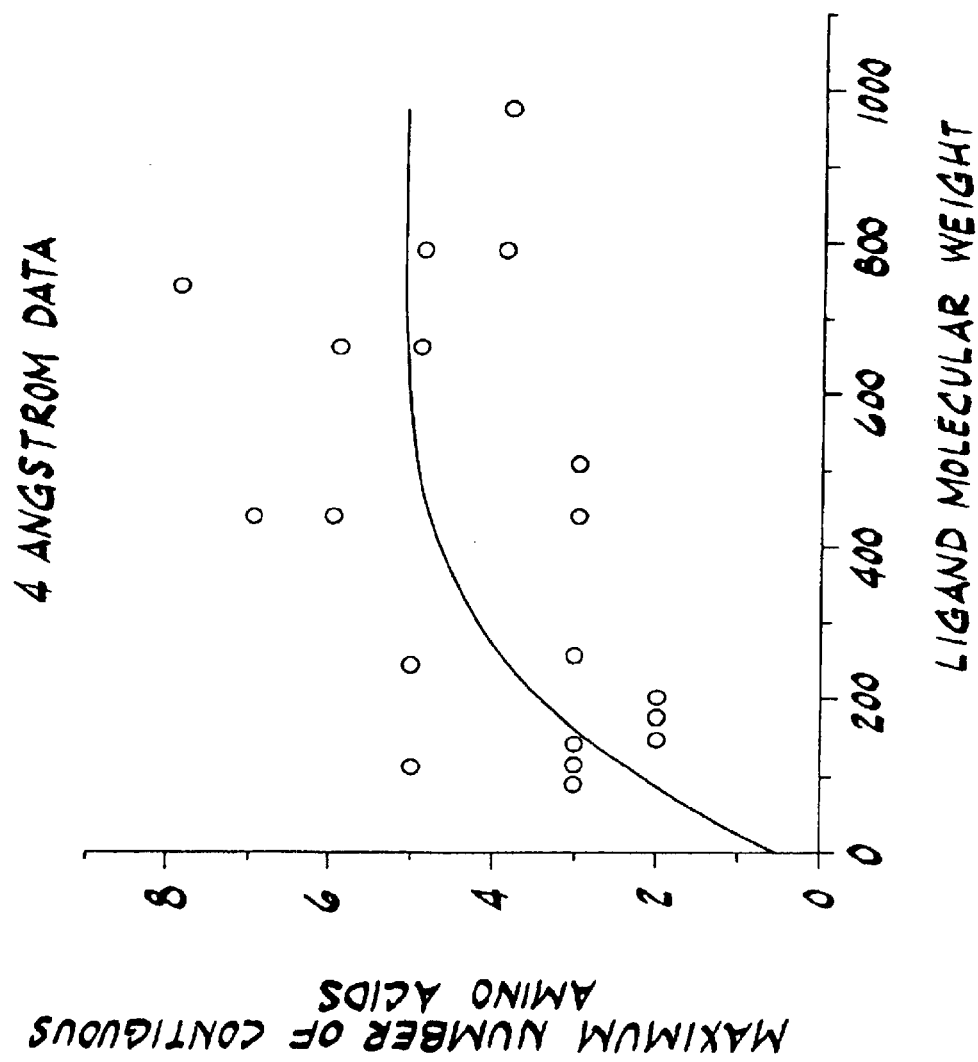

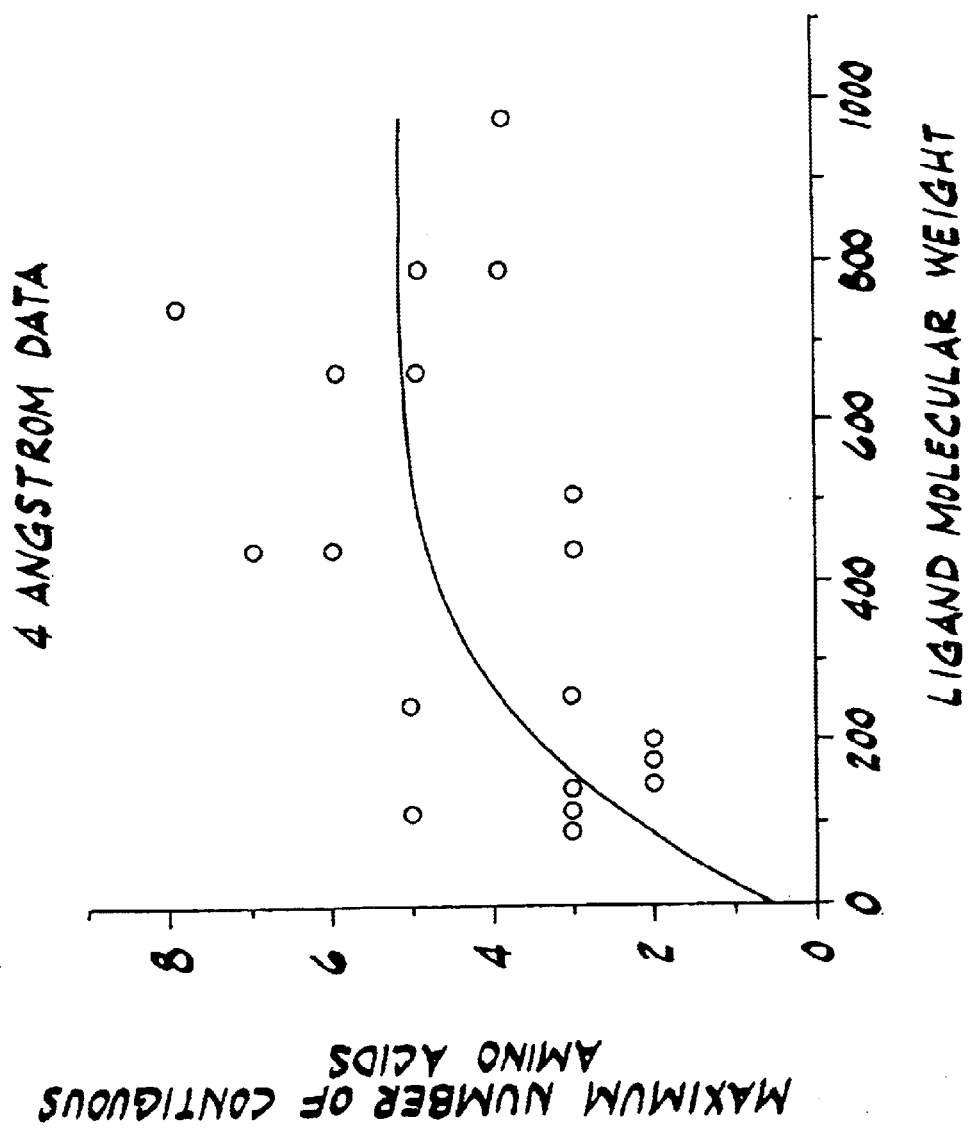

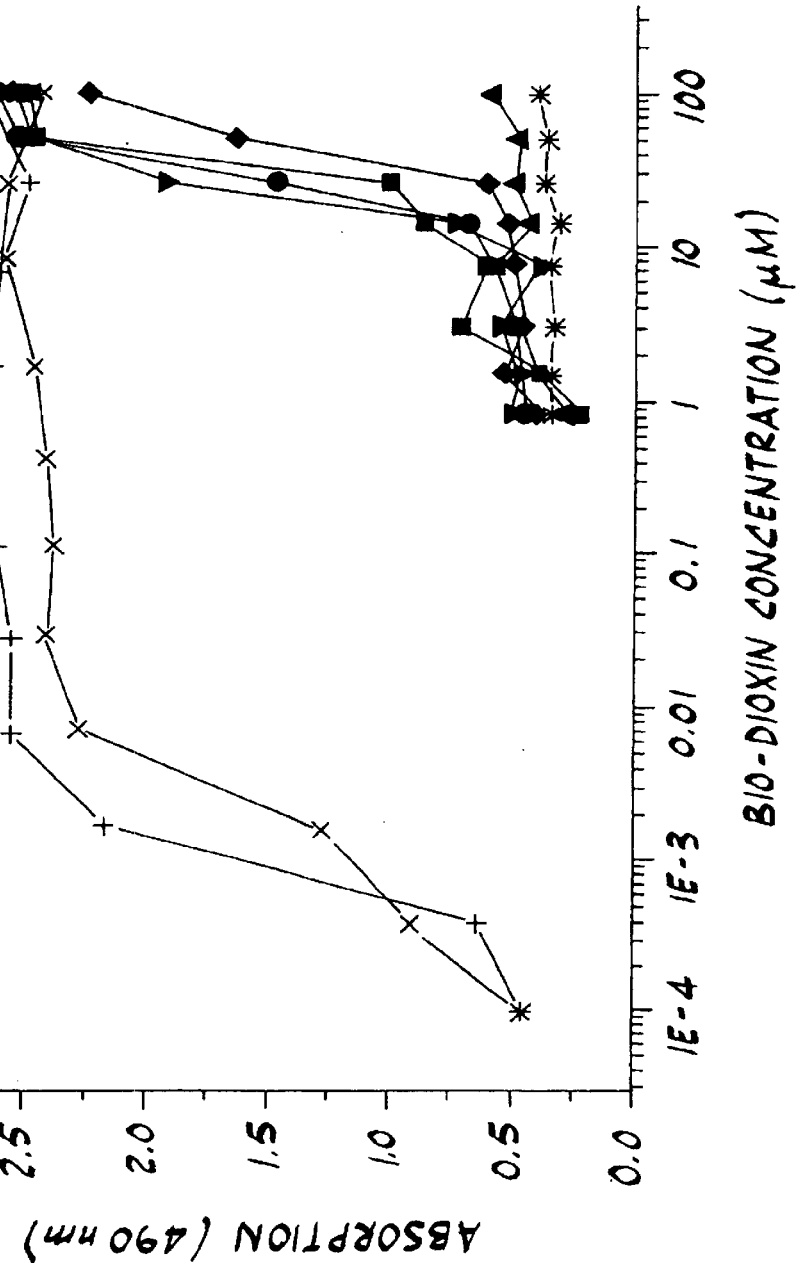

```
                            SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:1:

Thr Ser Pro Pro
1

(2) INFORMATION FOR SEQ ID NO:2:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:2:

Ser Pro Pro Ser
1

(2) INFORMATION FOR SEQ ID NO:3:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:3:

His Thr Pro His Pro
1               5

(2) INFORMATION FOR SEQ ID NO:4:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide
```

(xi) SEQUENCE DESCRIPTION: SEQ ID NO:4:

Ser His Pro Ser Thr
1               5

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Glu Pro Phe Pro
1

IDENTIFICATION OF MOLECULAR TARGETS

This application claims the benefit of U.S. Provisional Application No. 60/051,780, filed Jul. 7, 1997.

BACKGROUND OF THE INVENTION

The present invention is directed, in general, to a method for the identification of the molecular targets for drugs or toxins in an organism or other biological system.

Most drugs or toxins express their activity by binding to proteins. These proteins are referred to as receptors, drug targets or molecular targets (Gies, 1996). Drugs (pharmaceuticals), toxins and other biologically active molecules will be referred to herein as ligands. Identification of the ligand target is the crucial first step in understanding how a ligand affects a biological system. Currently, this identification is usually a long and arduous process. The identification of a ligand's target is desirable, however, because it provides essential information for the improvement of the drug or assessment of toxicity or side effects.

Many drugs are now designed specifically to bind to a particular target protein, and their primary target is not in doubt. However, it is possible for these drugs to have additional targets to which they bind that give rise to unexpected or unwanted biological effects (toxicities or side effects). The origin of these side effects or toxicities is not always clear from the primary mode of action of the drug. Identification of secondary targets, the interaction with which leads to side effects, may aid initial toxicological evaluations on humans by identifying potential biological systems to monitor, aiding in the interpretation of observed adverse effects, or providing information that could be used to counteract these effects.

In addition to designed drugs, natural products or synthetic organics are often screened for a particular biological activity (e.g., killing of human cancer cells in culture), and those displaying desirable activities are identified and developed without foreknowledge of the molecular target through which its activity is derived. The first step in understanding the mode of action of these drugs is to determine the molecular target of the drug. This is often a slow and expensive process. However, identification of the primary and secondary targets of these types of drugs is crucial to their further development and toxicological evaluations.

Prior to human testing of a new drug, a drug is tested on animals to evaluate its toxicity. The success of these toxicological screens depends on the efficacy with which the animal model mimics the human systems to be effected. If the molecular targets of the animal are essentially identical to those of humans, the toxicological evaluation in an animal will be an accurate guide to the toxicity of the drug in humans. This is, however, not universally true. Many drugs and toxins are highly species dependent in their action (for instance, aspirin is toxic to mice, Ohdo, et al., 1995). If a list of potential human molecular targets were available prior to testing in animals, one could choose a more appropriate test animal. For instance, if one potential target of a drug is the enzyme hexokinase (the first enzyme in the glycolytic pathway), the sequences of human and mouse hexokinase could be compared; if these sequences are similar at the postulated drug binding site then a mouse is an acceptable model for the evaluation of the effect of a drug on glycolysis; if not, then use of another animal model would be indicated. Consequently, the ability to predict potential drug binding sites in advance of animal testing would aid in the design and evaluation of toxicological screens. Furthermore, during clinical trials, a list of potential targets would simplify the evaluation of adverse effects of the drug.

There have been instances during the clinical use of a drug where unexpected benefits have been observed, identifying a drug being used to treat one pathology as efficacious against another one. This is particularly advantageous since a drug in clinical use has already passed through many regulatory hurdles and completed toxicological evaluations. A list of potential targets for a drug already in use could provide clues to new applications of the drug, and provide lists of pathologies against which the drug should be tested. This would be particularly beneficial for rare diseases where there is little financial incentive for drug development.

In addition to the determination of the mode of the desired interactions of pharmaceuticals, the identification of molecular targets is also essential in understanding the effects of environmental toxins. Man-made and naturally occurring toxins present a continual danger to human populations. Assessment of the risks posed by these molecules is dependent on determining the mode of action of the toxins. Further, these molecules may, in some cases, have several independent physiologically important targets. A complete characterization of the risk associated with exposure to these toxins involves identification and characterization of all relevant molecular targets.

Current methods of identifying the molecular targets of drugs or toxins in biological systems are cumbersome. Usually, they involve culturing large amounts of mammalian or other organismal cells in order to harvest enough protein extract to test for binding to the ligand of interest. Once these proteins are extracted, they must be isolated in sufficient amounts for protein sequencing by affinity to the ligand (a difficult task for low-expression proteins). Then, the purified protein must be partially sequenced by Edman degradation and a putative peptide sequence determined. If this sequence is of sufficient quality, then a set of degenerate DNA hybridization probes must be devised to screen the genomic library of the original cell of interest. If this process is successful, then the gene for the protein may be recovered, cloned into an expression vector, and later sequenced. Although this process will yield the identity of the protein suspected of binding to the ligand, the steps of cell culturing, purification, peptide sequencing, and probing for hybridization of the gene of interest, are all costly and time consuming.

Sparks et al. (1996) and Hoffmann et al. (1996) reported that they screened human and mouse protein libraries generated from cDNA to identify proteins with high affinity for specific peptides. They have described only screens against peptides (not, e.g., small molecule drugs or toxins). Also, random peptide libraries are sold commercially for screening against antibodies to identify epitopes (New England Biolabs Product Catalog, "Ph.D" products, 1998), another form of protein—protein interaction. Screening for proteins that demonstrate high affinity for peptide ligands is both conceptually and practically different from using small molecules as ligands. Protein-protein interactions generally involve the spacio-chemical interaction of large structures on each protein, generally encompassing relatively large sites of interaction. Thus, binding energy is ordinarily much stronger for peptide ligands. However, the applications of this technique are relatively limited, as many biologically active molecules of interest are not proteinaceous.

SUMMARY OF THE INVENTION

Among the objects of the invention, therefore, is the provision of a process for the identification of potential molecular targets for drugs, toxins or other small biologically active molecules.

Briefly, therefore, the present invention is directed to a process for the identification of a protein which binds to a ligand, the ligand having a molecular weight which is less than 5,000 Daltons and being other than a peptide or protein. In the process, the ligand is screened against a library of peptides or proteins each of which is displayed on the surface of a genetic package that contains the corresponding nucleic acid sequence to identify the members of the library which have an affinity for the ligand which is greater than the affinity possessed by other members of the library. Each member of this peptide or protein library is physically linked to a nucleic acid polymer which encodes that member by a genetic packages, which also allows the peptide or protein to interact with the ligand. Those members of the library which have an affinity for the ligand which is greater than the affinity possessed by other members of the library are separated from the library and the nucleic acid sequences which encode these members are determined and translated into peptide sequences or consensus peptide sequences. Proteins which contain the peptide sequences or which correspond to the consensus peptide sequences are then identified by searching protein sequence databases.

Other objects and features of this invention will be in part apparent and in part pointed out hereinafter.

DEFINITIONS AND DESCRIPTIONS OF FIGURES AND SEQUENCE IDENTIFICATIONS

"Ligand" as used herein means a small molecule (under 5 kD) which is capable of binding to a protein, preferably other than a nucleic acid, peptide or protein.

"Peptide" as used herein means an unbranched amino acid polymer, ranging in size from 3 amino acids (the lowest number for which consensus sequence information would be useful) to any length. Some very long peptides, as defined here, would sometimes be referred to as "proteins" by persons skilled in the art.

"Genetic package" as used herein means any mode of connecting a protein fused with a peptide from a peptide library with the genetic information encoding the peptide fused, while presenting that peptide in such a manner that it may interact with a ligand of interest. A non-exhaustive list of genetic packages includes: phage peptide presentation systems, bacterial pilus presentation systems, yeast surface protein presentation systems, plasmid DNA binding fusion protein systems, and other like modes.

"Plating agent" as used herein means any molecule which can be used to fix a conjugated molecule to a solid support, including molecules which comprise a solid support.

"Amplification" as used herein means the replication of the genetic package displaying a member of a peptide library and containing DNA encoding that member of the library.

"Taxane" as used herein denotes compounds containing the A, B and C rings (with numbering of the ring positions shown herein):

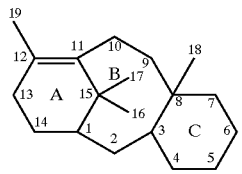

BRIEF DESCRIPTION OF THE DRAWINGS

FIGS. 1A and 1B show the number of amino acids in contact with a bound ligand for selected proteins, as determined an analysis of their three dimensional structure, with a "contact" criteria of a maximum separation of 4 angstroms and 5 angstroms.

FIG. 4 shows the results of the dioxin binding ELISA experiments of example 3.

Figure 1B:
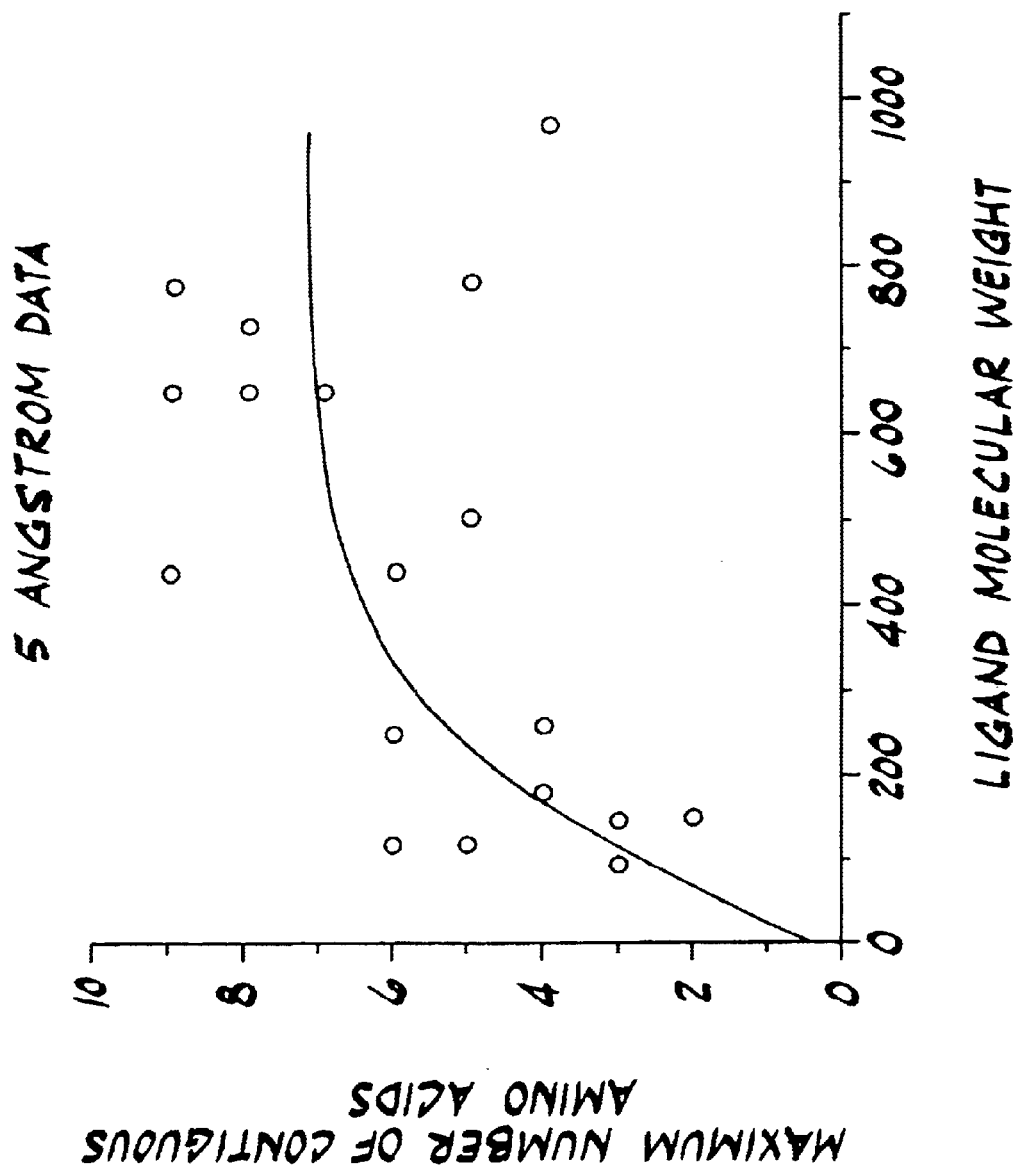

SEQ ID NO. 1 lists the sequence of a tetramer consensus peptide sequence identified from the second round of affinity selection enrichment in example 1.

SEQ ID NO. 2 lists the sequence of a tetramer consensus peptide sequence identified from the second round of affinity selection enrichment in example 1.

SEQ ID NO. 3 lists the sequence of a pentamer consensus peptide sequence identified from the second round of affinity selection enrichment in example 1.

SEQ ID NO. 4 lists the sequence of a pentamer consensus peptide sequence identified from the second round of affinity selection enrichment in example 1.

DETAILED DESCRIPTION OF THE PREFERRED EMBODIMENTS

The action of a ligand on a molecular target is dependent on its energy of interaction with the target, or binding energy. This is usually characterized as a binding constant or a dissociation constant. Herein, the concept of a dissociation constant is used. For the dissociation of a protein-ligand complex, PL, into a ligand, L, and a protein, P, $$PL \text{-----------} > P+L \tag{1}$$

the dissociation constant, $K_D$, is defined as, $$K_D = [P][L]/[PL] \tag{2}$$

wherein [P] and [L] are the concentrations of protein and ligand, respectively, and [PL] is the concentration of the protein-ligand complex. The most intuitive characterization of $K_D$ is that it corresponds to the concentration of ligand at which half of the proteins retain bound ligand. Physiologically relevant binding constants are generally smaller than 10–50 micromolar, and are often in the nanomolar range.

Small molecules bind to the accessible surface of a protein, usually in a pocket or groove where the contact area between the ligand and the protein will be larger; the larger the contact area, the greater the number of bonds that can be made between the ligand and the protein, and the smaller the dissociation constant. If ligand binding induces substantial conformational change in the protein, the ligand may become deeply embedded therein. A protein, of course, is a polypeptide chain consisting of an unbranched polymer of amino acids. To form a native conformation, the protein chain folds into a complex structure in which amino acids from different portions of the amino acid chain interact with one another. Usually, but not always, the binding site is made up of amino acids from several different regions of the protein chain. Sometimes the presence of the ligand can stabilize disordered portions of the protein chain as it wraps around the ligand. Consequently, in most cases, no more than a few contiguous amino acids are in contact with a small ligand when it is bound to a protein in its native conformation.

It is useful to distinguish the amino acids that make up the binding site for the ligand and form the interactions between the protein and the ligand, from those that form the scaffolding around the binding site. These amino acids help to create the site, but have no direct interaction with the ligand. The binding site amino acids will not necessarily display particular affinity for the ligand unless they are supported in the proper scaffold. Consequently, the proper scaffold is required for the construction of a binding site, or a mimic of a binding site.

In a preferred embodiment of the present invention, the first step in the identification of potential ligand targets is the screening of peptide or protein libraries for sequences that exhibit relatively high affinity for a particular ligand compared to other sequences in the library. Most protein or peptide libraries are expressed on the surface of a genetic package which provides a base protein on which the library peptide is presented.

A protein or foreign peptide may be displayed on the surface of a phage, bacterium, yeast cell or other genetic package through the insertion of nucleic acid corresponding to the sequence of the peptide or protein into the genome (DNA or RNA) of the genetic package or vehicle of choice. In order to screen a library of peptides for binding with the ligand of interest, a physical or logical connection between each peptide and the nucleic acid that encodes the peptide is desirable. Usually, this is accomplished by fusing the DNA sequence corresponding to a peptide with the gene encoding a surface protein of the genetic package. If the alteration to the surface protein does not prove deleterious to the biological system on which it is displayed, a genetic package with a foreign protein or peptide on its surface may be propagated. After rounds of screening for affinity to the ligand of interest and reculturing bound candidates, such a connection allows identification of the genetic material encoding interesting peptides. Once proteins or peptides with the desired binding properties are obtained, their sequences can be obtained by sequencing the corresponding nucleic acid within the genetic package. The sequences thus identified may correspond to sequences within proteins that bind to the ligand. To optimize the probability of obtaining positive results, several libraries representing numerous scaffolds should be used.

Although display on a variety of different genetic packages has been accomplished, most of the work has involved bacteriophage particles. The concepts involved in construction and screening of libraries will be introduced here using the example of phage as a vehicle, but this does not exclude other genetic packages. Other types of use in the invention include DNA binding fusion protein systems, and yeast membrane fusion protein systems. The use of other protein or peptide library display systems is well understood in the art, and the choice of which specific display system to use will hinge mainly upon issues of convenience for the particular investigator.

Several phage based systems for presenting a peptide on the surface of phage are described in the literature. The fusion phage approach of Parmley and Smith, 1988, Gene 73:305–318, has been used to display proteins. Others have described phage based systems in which the peptide is fused to the p3 coat protein of filamentous phage (see Scott and Smith, 1990, Science 249:386–390; Devlin et al., 1990, Science 249:404–406; and Cwirla et al., 1990, Proc. Natl. Acad. Sci. USA 897:6378–6382; each of which is incorporated herein by reference. In addition, see the discussion of phage fusion techniques in Schatz, P. J., et al., U.S. Pat. No. 5,498,530. These later references describe the fusion of the peptide at the amino terminus of the p3 protein.) The connection between the isolated peptide and the genetic material that encodes the peptide is established, because the fusion protein is part of the capsid enclosing the phage genomic DNA. Phage encoding peptide ligands for receptors of interest can be isolated from peptide-displaying libraries after several rounds of affinity enrichment followed by phage growth.

By inserting different nucleic acid sequences into each phage genome, it is possible to construct libraries consisting of billions of different phage particles, each displaying a different peptide or protein (Scott and Smith, 1990). The diversity of the libraries is limited by censorship of sequences that are deleterious to the biological system of choice, by the length of the inserted peptide or protein (i.e. greater diversity can be achieved by 12 amino acid-length insertions than by 4 amino-acid-length insertions), and by the practicalities of handling very large numbers of phage particles. By using a number of independently generated phage libraries in parallel experiments, the later limitation can be lessened.

Libraries can be constructed in a number of ways known in the art, and two will be described in some detail here. The first are random peptide libraries, like that used in example 1. In this case, all, or a portion of, the nucleic acid inserted into the phage genome is randomized (e.g. by chemical synthesis of partially or completely random oligonucleotides then inserted into the genome). This technique is typically used to generate 5–12 random amino acids on the surface of a phage particle.

Several methods exist for generating DNA sequences encoding a random peptide library. One of the most common consists of generating DNA oligomers of synthesized trinucleotide codons. These nucleotide trimers may be facilely synthesized using a solid-support method (See, McBride and Caruthers, 1983, Tetr. Letters 22:245). The trimers are then mixed at the desired molar ratios and utilized as the building units in solid-support DNA synthesis. The ratios will usually be approximately equimolar, but may be a controlled unequal ratio to obtain over- or under-representation of certain amino acids coded for by the oligonucleotide collection. The condensation of the trimers to form the oligocodons is done essentially as described for conventional synthesis employing activated mononucleosides as building blocks. See generally, Atkinson and Smith, 1984, Oligonucleotide synthesis (J. J. Gait, ed.), pp. 35–82. This procedure generates a population of oligonucleotides for cloning that is capable of encoding an equal distribution (or a controlled unequal distribution) of the possible peptide sequences, and minimizes the accidental synthesis of stop codons. Schatz, et al., U.S. Pat. No. 5,498,530.

Screening a random library requires sequencing of a large number of clones in order to identify a consensus sequence appearing in several clones. The multiple appearance of a sequence or similar sequences in clones isolated from a random library is required to distinguish a sequence with high affinity relative to the remainder of the library from one with relatively low affinity that has been isolated by chance due to, for instance, non-specific binding during affinity selection. Identification of commonly occurring sequences which are the result of desirable growth properties as opposed to desirable binding properties can be accomplished by the statistical analysis of one hundred randomly chosen members of the library. Computer software which screens these one hundred random sequences with over twenty amino acid property scales (including such properties as hydrophobicity, flexibility, etc.) detects inherent biases in each library and identifies library members which predominate in number due to advantageous growth properties.

The consensus binding sequence identified by screening of random peptide libraries does not, usually, constitute the entire random insert. The remainder of the randomized insert provides for variation in the scaffolding around the consensus sequence and/or completion of the binding site. For instance, a 5 amino acid consensus embedded in a 12 amino acid insert will be attached to as many as $8 \times 20^7$ ($1.024 \times 10^{10}$) possible scaffolds in the library. This suggests that with the use of a wide variety of libraries with peptide presentations including both linear and cyclized configurations, a pentapeptide can be displayed in an extraordinarily large number of conformations. Some of these could correspond to the conformation that it adopts on the surface of a protein that constitutes a natural target for the ligand.

A second method for constructing libraries is to insert DNA from a cDNA library. A cDNA library is constructed from the messenger RNA within a particular tissue, and may even be constructed by PCR from a single cell. The mRNA is isolated from the tissue, and a reverse transcription is used to synthesize the DNA that corresponds to the sequence of the mRNA. For a cDNA insert library generation protocol, see Mierdorf, et al., U.S. Pat. No. 5,629,179. Inserted into a phage genetic package, this gives rise to a library of phage with surface displayed peptides having the same sequence as proteins or fragments of proteins from the tissue used to isolate the mRNA. cDNA libraries are censored by the same mechanisms as random peptide libraries. Some inserts, particularly the larger ones (e.g. Rodi and Makowski, 1997), may be fatal to the biological system being used; some inserts will not fold into the conformation of the native protein, making their binding properties irrelevant; and others can constitute fragments of protein that may or may not exhibit native binding properties.

Successful screening of a cDNA library provides a list of potential target proteins, all of which correspond to complete, expressed proteins. When the sequence of the identified protein is in the sequence data bases, the information about binding will add to the information already known about the protein. When the protein sequence is not in the data base, the sequence will represent the identification of a new protein. False positives can arise from misfolded proteins binding to ligand in non-physiological ways and proteins that bind non-specifically to the ligand. False negatives can arise from proteins that are misfolded and do not bind in their normal physiologically relevant fashion, from proteins not represented in the library due to non-expression at the time the mRNA was reverse-transcribed, and from proteins that are censored from the library because they are fatal to the system expressing them.

Successful screening of a random peptide library will result in the identification of one or more consensus sequences that exhibit affinity to the ligand. Proteins that are already characterized and contain this sequence will be identifiable by a search of the sequence data banks such as GenBank and SWISS-Prot. Some of the identified proteins will contain the consensus sequence in a conformation that will not bind the ligand; these are false positives. Other proteins may display the sequence in a manner that does bind to the ligand. These ligand-binding proteins can exhibit binding constants that may or may not fall within the range of physiological relevance. False negatives will occur for all proteins not yet sequenced and placed in the data bases: however, the number of false negatives will decrease substantially as the work of the Human Genome Project continues. Other false negatives will occur when the libraries that are screened do not adequately mimic the environment of the ligand binding site in a protein.

Using a cDNA library has both advantages and disadvantages over random libraries. Every clone isolated in the screen corresponds to a protein, so the number of irrelevant sequences obtained is small. And usually the cDNA library can give you the entire sequence of the protein target. However, only proteins being actively expressed in a cell have a chance of being detected in the screen; an unknown number of proteins will fold incorrectly on the surface, and not be detected (or provide false positives); membrane proteins or proteins that form large macromolecular assemblies are unlikely to fold properly on the phage surface; and proteins from other species, early development proteins or rarely expressed proteins would each need to be screened for with different libraries. Selection of the proper cDNA libraries for drug or toxin screening can be guided by knowledge of the physiological effects of the drug or toxin and/or known target organs. Because of the smaller peptides displayed in random peptide libraries, precise folding of their short sequences is unnecessary to isolate consensus sequences of interest: the amino acids involved in ligand binding are displayed in a wide variety of molecular scaffold environments, any of which might correspond to the correct molecular context for binding. A further advantage of screening a random peptide library compared to a cDNA library is that it provides information about the binding site as well as the protein involved.

Peptide libraries displayed on a genetic package can be screened for peptides that display a relatively high affinity for a particular ligand by a variety of affinity purification processes including biopanning (as used in example 1)(Kay et al., 1996; Yu, Y., et al., 1996, Methods Enzymol. 267:3–27; Petrenko, V. A., et al., 1996, Protein Engineering, 9:797–801), column chromatography, Southern and Western blotting, and electrophoretic techniques. The advantage of physically connecting the displayed peptide to the nucleic acid coding for it is that, at least in principle, the isolation of even a single particle that binds to the ligand is adequate for detection, since the genetic package on which it is displayed can be used to grow up large amounts of identical particles for characterization. Therefore, isolation of clones with particular affinity for the chosen ligand provides the opportunity to determine the sequences of the peptides or proteins displaying that affinity. Once genetic packages displaying peptides with the desired binding properties are isolated, their sequences can be obtained by sequencing the corresponding nucleic acid within the genetic package. The sequences thus identified may correspond to sequences within proteins that bind to the ligand. To optimize the probability of obtaining useful results, several libraries should be used.

The number of positives that a particular sequence will identify can be estimated. A given pentapeptide sequence will occur roughly once in every 3.2 million amino acids. Given an average protein size of 500 amino acids and 75–100,000 proteins in the human genome, one can expect about 16 occurrences of a particular pentapeptide. Since some sequences are far more common than others, as proteins have not evolved in a random fashion but as repetitions and modifications of pre-existing genetic units or elements, the number of proteins containing a consensus sequence could easily be twice that or substantially less. Still, even once the entire human genome is sequenced, screening by a random peptide library will rarely result in an unwieldy list of human proteins containing the sequence.

Kabsch and Sander, Proc. Natl. Acad. Sci. USA 1984, Feb; 81(4):1075–1078 searched 62 related proteins with 10,000 residues and identified 25 cases where the same pentapeptide appeared in two unrelated proteins. In 6 of the 25 cases the same five residues were in an alpha helix in one protein and in a beta sheet in another. Nevertheless, in many cases the structural similarities between pentapeptides of identical sequence were significant. Minor and Kim (1996) demonstrated that an 11 amino acid sequence could be made to fold into an alpha helical conformation when inserted into one position of a protein and into a beta-sheet conformation when inserted into another position. This suggests that the same sequences may be displayed in very different conformations in different proteins and indicates that to have a good chance of identifying a drug target it will be necessary to screen multiple libraries in order to identify the binding motif.

The limitation in most previous work involving peptide display libraries was that they were screened only for affinity to a protein; the invention concerns screening for affinity to a small molecule ligand (drug, toxin). This difference is operationally quite large since the dissociation constants we work with are much larger (lower affinities) and therefore more difficult to detect. The difference is philosophically quite large, since the properties of drug and toxin binding sites were thought to make this approach impractical.

Our search of the Protein Data Base of three-dimensional structures, however, identified several hundred unique structures with bound ligand and known three-dimensional structure. An analysis of these structures indicated that for nearly all ligands with molecular weights over 300 Daltons, at least one stretch of 5 or more continuous amino acids was involved in binding directly with the ligand (See FIG. 1). The graphs show the number of contiguous amino acids in "contact" with bound ligands, based on three dimensional structure data gathered for several proteins. "Contact" has been defined as either being less than 4 angstroms or 5 angstroms from the ligand. As would be expected, a larger number of amino acids are in "contact" with the ligand when the 5 angstrom criterion is used. However, the maximum average number of contiguous amino acids does not exceed eight, even under the 5 angstrom standard. For particularly large ligands, the number saturates at between 7 and 10; larger binding sites are most commonly made up of more loops of discontinuous amino acids, not larger loops. It is unusual for a ligand binding site to be made up of only a single stretch of amino acids. Therefore, any identified stretch of continuous amino acids that participates in a ligand binding site will constitute only a partial binding site. Consequently, the portion of the binding site constituting the longest stretch of continuous amino acids will have relatively weak affinity for the ligand in the absence of the remainder of the binding site residues. However, we have demonstrated in Example 1 that the ratio of specific to non-specific binding is adequately strong to be detectable relative to other peptides in a library.

When analyzing the peptide sequences selected for utilizing the claimed method, strong consensus sequences may emerge. In this case, the investigator may preferably utilize one of the many public-domain search engines (for instance, a BLAST search of GenBank) to find sequences of proteins which contain the consensus sequence or one similar to it. This technique was applied when analyzing the consensus sequences of examples 1 (SEQ. ID NO. 3) and 3 (SEQ. ID NO. 5).

However, in the absence of a clear consensus sequence, the selected peptides still contain information useful for the identification of potential binding sites in proteins. Utilization of this information may preferably be effected by programming a computer to perform the following algorithm to score the homology between the selected peptides and sequences of proteins that are suspected of being involved in a particular molecular activity (toxic or therapeutic, as the case might be). For instance, the taxol-selected peptides were scanned against all proteins known to be involved in apoptosis. Even removing the two peptides containing HTPHP (Seq. ID No. 3) from the set of taxol selected peptides from example 1, this algorithm can identify the flexible loop of Bcl-2 as the site of taxol binding because it has higher homology to the selected peptides than other places in other proteins known to be involved in apoptosis.

The algorithm is a simple brute force comparison of the sequence of a protein with all the selected peptides AND a control set of random (non-selected) peptides from the same peptide library. The randomly selected peptide control is needed because most libraries have preferences for amino acid pairs and triplets that will lead to false positives if a control group of peptides is not used. For instance, the NEB 12mer library used in example 1 has a preference for pairs of prolines (PP). The pairs of prolines found in the taxol-selected peptides are therefore, not necessarily due to taxol selection, but rather to their preference in the library. If by some coincidence, a ligand had high affinity to the sequence PP, then the selected peptides would have a frequency of PP that would be greater than that of the random (control) peptides.

An important consideration in programming the algorithm for comparison is the determination of the means of comparing the sequences of the peptides with the sequences of proteins. This requires selection of (i) the length of the segment on which a comparison will take place (how many amino acids will be considered at one time); (ii) the means by which a homology score will be calculated (this usually involves selection of an amino acid similarity matrix); and (iii) the homology below which a peptide or peptide fragment will be considered to be unrelated to the protein sequence to which it is being compared.

For (i), the comparison is preferably made over a peptide length relevant to the binding of a ligand. In investigation of the binding of a peptide to a small ligand, only 4–8 amino acids are likely to be involved in binding. Use of less than 4 amino acids would lead to too many false positives—a very noisy output; use of more than 8 amino acids would lead to too many false negatives. In most cases 6 amino acids were used at a time, although 5 or 7 may be preferable for other applications.

For (ii), choosing the right homology matrix, or amino acid similarity matrix is helpful for scoring the similarity between two amino acid sequences (Dayhoff, M. O., et al.) Applicants have used several different homology matrices for these calculations and found that they all give similar results, but produce results with varying signal to noise ratios. Different matrices may be preferable in different circumstances. The typical matrix is 20×20, one row and one column for each amino acid. Additional rows and columns can be added for special purposes or to enhance certain types of homology searches. The diagonal of the matrix scores identities (e.g. when an alanine is matched with an alanine). The diagonal usually has different scores for different amino acids (e.g. tryptophan is very seldom substituted for by anything else, so its diagonal score will be higher than, for instance, alanine, which can frequently be substituted without seriously altering protein structure or function.) The off-diagonal elements of the matrix show similarity scores. For instance, alanine and serine have a low positive score, but tryptophan and serine have a significant negative score. Applicants have used a homology matrix called Blossum62 (Henikoff, S. et al., 1992) in their comparisons.

For (iii), the preferable noise level has been determined entirely empirically using Bcl-2 as an example and other apoptosis-related proteins as controls. The absolute number depends on the similarity matrix being used.

The algorithm may be characterized by the following steps:

(a) Choose the first block of the protein sequence (e.g. the first 6 amino acids).

(b) Choose the first block of the peptide sequences (e.g. the first 6 amino acids of the first peptide).

(c) Use the similarity matrix to calculate the homology score between the block of the protein and the block of the peptide. This is done by summing the matrix elements that correspond to the pairs of amino acids made up of one from the protein and the corresponding amino acid in the peptide.

(d) Advance the comparison data set to the second place in the first peptide, and repeat (c).

(e) Advance through all possible positions in all the peptides selected by the affinity screen, repeating (b) through (d) for each peptide.

(f) Once this comparison is completed with all peptides selected, advance to position 2 in the protein and repeat steps (b) through (e).

(g) Repeat steps (b) through (f) for all positions in the protein while storing the cumulative homology score for each position.

(h) Carry out steps (b) through (g) for a control (random) set of peptides selected from the library.

(i) Subtract the homology score for the random peptides from that of the selected peptides for each position in the protein.

(j) Output the results of the calculations.

The maximum homology score obtained by this algorithm for any given protein is a measure of its possible involvement in the binding of the relevant ligand. The distribution of the homology score throughout the protein provides information about the position where the binding may be taking place. In the instance of Bcl2, this demonstrated that the binding of taxol involved an extended region of the flexible loop of the protein, even without the inclusion of the SEQ. ID NO. 3 containing peptides in the data set.

Following the discovery of human Bcl-2 as a potential molecular target of taxol, and the confirmation of binding of Bcl-2 to taxol with micromolar affinity, the applicants have devised a method for determining the apoptotic activity of taxanes, based on their binding to Bcl-2. The method involves simply measuring the dissociation curve of the taxane/Bcl-2 complex, using a standard ELISA assay. Taxanes which bind more strongly to Bcl-2 than taxol may induce apoptosis in cancer cells with more efficacy than taxol, and thus make better pharmaceutical agents.

The following examples illustrate the principles and advantages of the invention.

EXAMPLE 1
Identification of Taxol Binding Peptides

Taxol is an anti-cancer drug with proven efficacy against a wide variety of malignancies, with those of most clinical interest being human breast and ovarian carcinomas (Rowinsky and Donehower, 1991). Its only known molecular target is tubulin which it induces to polymerize, disrupting the dynamic instability of microtubules in the mitotic apparatus and halting mitosis at the metaphase/anaphase transition (Jordan et al., 1993). A wide variety of other responses to taxol have been reported, including the induction of programmed cell death or apoptosis, an increased level of a number of intracellular messengers and growth factors including p53 (Roth, W. 1998), and the phosphorylation and subsequent inactivation of the anti-apoptotic protein Bcl-2 (Haldar et al., 1995; 1996). These activities are thought to be indirectly induced by the action of taxol on microtubules.

In an attempt to identify potential binding sites for taxol on β-tubulin or other proteins, a random phage-displayed peptide library was searched for peptides with high affinity for taxol. It was reasoned that a peptide with high affinity for taxol when exposed on the surface of a phage particle might also have high affinity for taxol when present on the surface of a cellular protein. A random dodecamer library displayed at the N-terminus of p3 of bacteriophage M13 (Ph.D.-12 library, available from New England Biolabs, Beverly, Mass.) was screened for members with high affinity for taxol. A taxol derivative biotinylated at the $C_7$ position was synthesized as described in Example 2. This taxol derivative was immobilized on the surface of streptavidin coated plates and standard techniques of biopanning were used to select for members with high affinity for the biotinylated taxol, with the following modifications. A ten-fold higher molar quantity of ligand (i.e. biotinylated taxol) was affixed to the streptavidin-coated culture dish than is normally used. Two independent screenings produced enrichment values (where enrichment=number of input phage/number of output phage) of $1.7 \times 10^5$ and $2.8 \times 10^5$ fold respectively. These taxol-binding phage were designated Round I. Twenty individual phage particles were selected at random from this Round I pool and subjected to nucleic acid sequence analysis. The remainder of Round I phage were amplified non-competitively so that taxol-binding peptides with low dissociation constants but poor growth properties would have a better chance of survival. Less than 90,000 plaque-forming units (pfus) were fixed in agar on 150 mm culture plates. Viral particles were eluted from the agar by gentle rotation of a solution of Tris-buffered saline plus 0.1%, TWEEN 20 (polyoxethylensorbitan manolaurate) (a non-ionic detergent) at 4° C. for approximately two hours. This viral suspension was purified and concentrated by two consecutive rounds of polyethylene glycol precipitation.

Amplified Round I clones were subjected to a second round of screening using a forty-fold higher amount of input phage onto the culture dish containing the conjugated taxol (to enrich for low $K^D$ or 'tight' binding phage particles versus non-specific binding phage particles), producing an enrichment of $5.1 \times 10^4$ fold. Amplification of these Round II phage particles, followed by a third round of screening with taxol (Round III) gave an enrichment value of $2.3 \times 10^4$ fold. Seventy members of the Round II and twenty three members of the Round III bacteriophage were selected at random and similarly subjected to nucleic acid sequencing.

Each group of peptides was analyzed in terms of amino acid sequence properties as follows:

Characterization of the sequence properties of the original library (i.e. prior to screening with taxol) was accomplished by calculating a Poisson distribution from the incidence of individual amino acids at each of the twelve positions for the random inserts. The information content of each clone was defined as minus the natural log of the inverse of its probability of occurrence within the library. This information content value is a convenient measure of probability, with larger information contents being associated with rarer sequences. The amino acid sequences of peptides isolated by affinity selection have relatively high associated information content compared to those from the parent library. The average information content increased from 33.1±1.6 for unselected phage (n=101) to 35.4±2.5 for Round I phage (n=20), 35.4±2.1 for Round II phage (n=70) and 34.8±2.4 for Round III phage (n=23). These numbers suggest that after Round I, affinity selection did not produce further enrichment for taxol-binding phage, and that after Round II growth characteristics became a measurable factor in the composition of the phage population, a scenario which has been hypothesized by other groups (Folgori et al, EMBO J. 1994 May 1; 13(9):2236–2243).

Sequence analysis of Rounds I, II and III were carried out to identify any bacteriophage which shared a minimum of three continuous amino acids out of twelve. All three rounds, as well as the randomly selected nonscreened phage, possessed pairs with continuous trimers in common. A control search using the 102 random nonselected sequences produced five tetramers, no pentamers, and one hexamer, the latter of which have information contents of only 30.2 and 31.0 respectively. Furthermore, a DELPHOS sequence search within the composite sequence database OWL (Bleasby et al. (1994) Nucleic Acids Research, 22(17), 3574–3577) using the control hexamer pulled out only two entries, a hypothetical human cytomegalovirus protein (ULB7 HCMVA) and a hypothetical yeast protein (S61023). Of the putative taxol-binding sequences, only the Round II sequences contained clone pairs sharing consensus sequences as long as four and five residues. Two tetramers, SEQ. ID NO. 1 and SEQ ID NO. 2, were identified amongst the Round II clones. Tetramers, however, are not specific enough to produce a manageable list of suspected target proteins in most cases at the present time. For example, a sequence search using SEQ. ID NO. 1 produced 873 matches, of which 152 were human sequences.

In addition to the two tetramers in Round II, two pairs of pentamers were identified. Clones TAX2.6 and TAX12.29 shared the pentapeptide SEQ. ID NO. 3 at identical positions within the insert peptide, and clones TAX2.8 and TAX2.74 shared SEQ. ID NO. 4 at different locations along the insert sequence. Localization of these four clones within indicates that TAX2.6 and TAX2.29 possess an information content of 35.9 and 36.3 respectively, whereas TAX2.8 and TAX2.74 possess information content values of 31.6 and 31.2 respectively. As information values are expressed as logarithms, these numbers show that the SEQ. ID NO. 3 match is a less likely statistical occurrence than the SEQ. ID NO. 4 match by a factor of about 10,000. After two rounds of biopanning, a single pentapeptide consensus sequence, SEQ. ID NO. 3, was identified as most likely corresponding to a taxol binding motif.

A search of the OWL database indicated that SEQ. ID NO. 3 does not appear in any known tubulin and is found in only two known human proteins, Bcl-2 (residues 55–59) and ataxin-2 (SCA2) (Pulst, et al., Nat. Genet. 1996 November; 14(3):269–276; Imbert et al., Nat. Genet 1996 November;14 (3):285–291). In Bcl-2 it appears in the middle of a highly flexible, 60 amino acid loop identified by comparison with the Bcl-2 homologue, BCl-XL, for which both x-ray crystallographic and NMR structures have been obtained (Muchmore et al., 1996). This loop acts as a regulatory domain in both Bc-XL and Bcl-2 (Chang et al., 1997) and is unnecessary for its anti-apoptotic activity (Muchmore et al., 1996). Because Bcl-2 function is known to be regulated by taxol, it represents a highly plausible molecular target for taxol.

Figure 2:
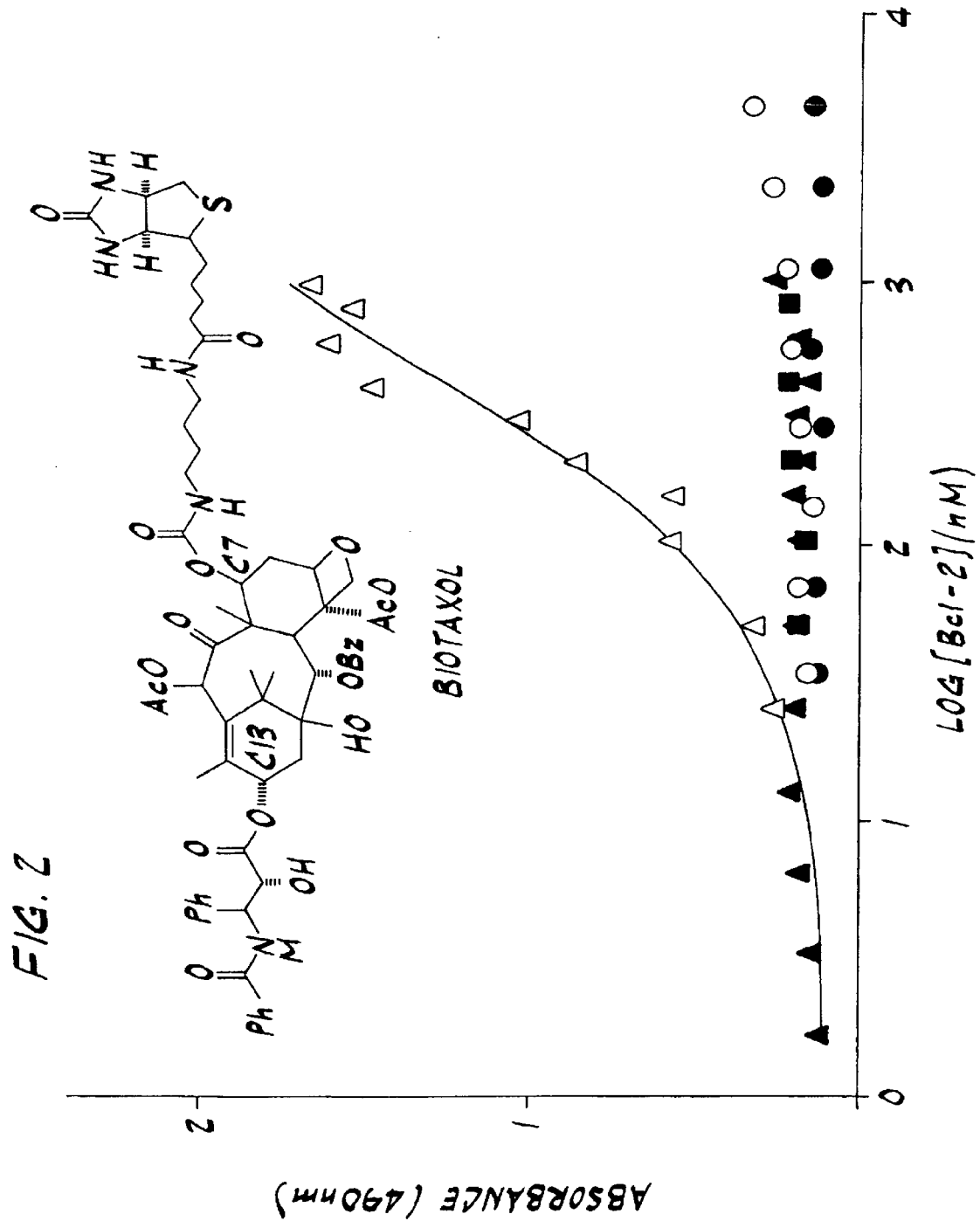
FIG. 2 shows the ELISA data demonstrating binding of Bcl-2/GST and Bcl-$X_L$ to taxol and various controls. Bcl-$X_L$ lacks homology to SEQ. ID NO. 3 in the putative binding site.

ELISA binding assays were used to determine if the Bcl-2/GST fusion protein binds directly to immobilized biotinylated taxol. Anti-Bcl-2 antibodies were used to detect Bcl-2 binding. These results demonstrate that Bcl-2 binds to the biotinylated taxol derivative with a $K_d$ of approximately 0.4 µM (see FIG. 2). The graph shows the ELISA data for the binding of the Bcl-2/GST fusion protein to taxol (open triangles), biotin (shaded triangles), and biotinylated dioxin (closed squares), as well as the binding of BCl-XL to taxol (open circles) and biotin (shaded circles). The x-axis is the log nM concentration of protein in solution (Bcl-2 or Bcl-XL); the y-axis is the uncorrected optical density at 490 nm. The insert is the chemical structure of the biotinylated taxol used in the selection of peptides. In similar experiments it was demonstrated that Bcl-2 also binds to biotinylated taxotere, at an approximately ten to fifty fold reduced affinity.

Figure 3:
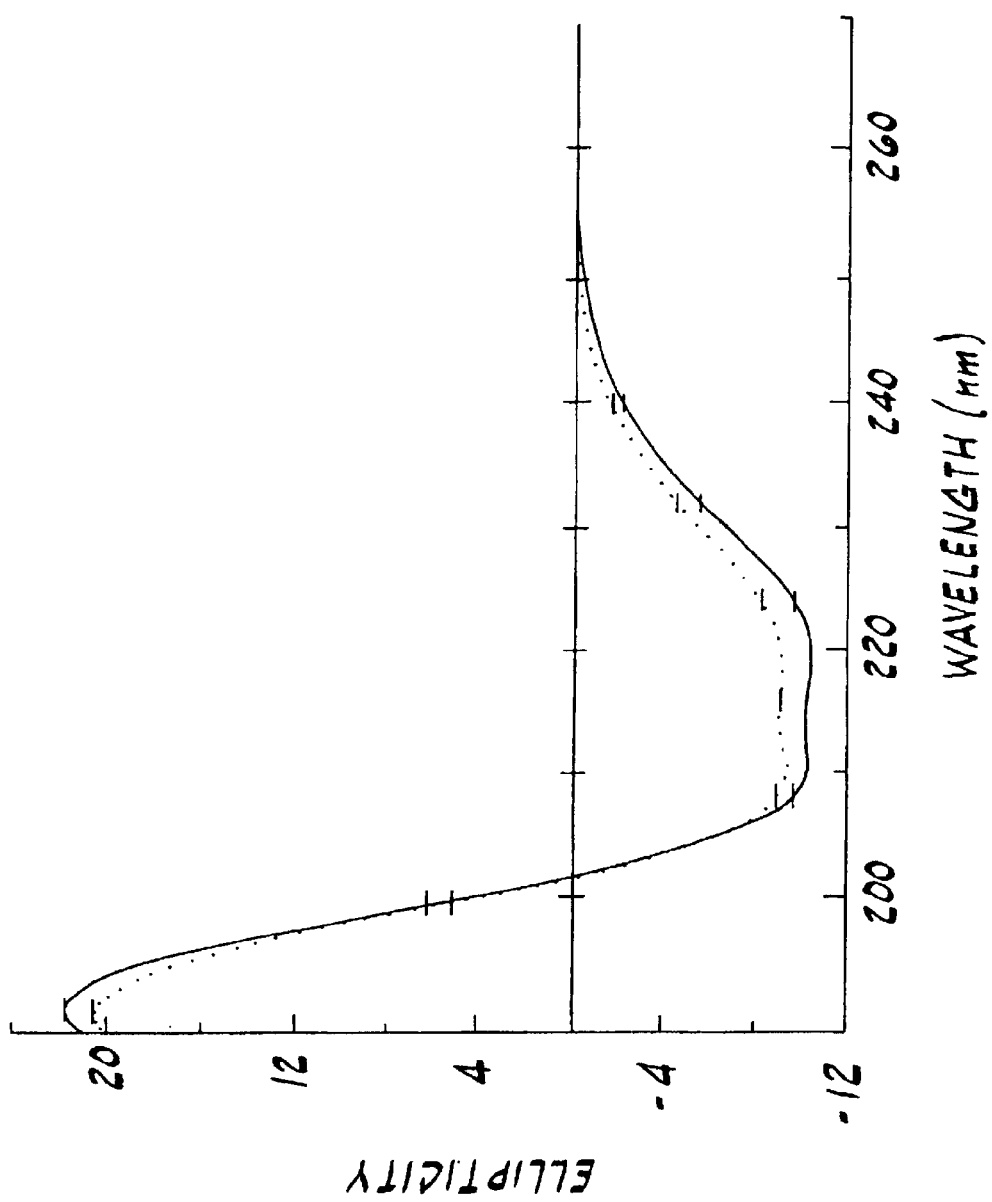
FIG. 3 shows the circular dichroism spectrum of Bcl-2/GST with and without taxol. This spectrum shows that the Bcl-2/GST fusion protein undergoes a substantial conformational change in the presence of taxol, unlike GST alone.

The binding of taxol to the Bcl-2 portion of the Bcl-2/GST fusion protein was corroborated by circular dichroism spectroscopy with the CD results demonstrating that the Bcl-2/GST construct undergoes a substantial conformational change upon binding taxol. The spectra of the fusion protein with and without taxol added are significantly different (see FIG. 3). The graph shows the circular dichroism spectrum of human Bcl/GST fusion protein with (solid line) and without (dotted line) taxol. Each spectrum is the averaged result of five spectra and subtracted baselines with standard deviations as indicated. These differences are much larger than the error bars (standard deviations) in the measurements, and involve a change in both the shape of the curve (ratio of the 220/210 nm peaks) and the peak positions. The secondary structures calculated for the Bcl-2 fusion protein with and without taxol differ by approximately 4%, and appear to involve a change in a region of the molecule that is found in a beta-turn conformation. This corresponds to the type of secondary structure which is predicted for the HTPHP-containing portion of the Bcl-2 loop region (SEQ. ID No. 3). The magnitude of the difference (mindful of the error levels) would suggest that approximately ten to twelve amino acids are involved in the change. Homology between TAX2.29 and human Bcl-2 lies between positions 1 through 12 and residues 55 through 66 respectively, inferring a minimum drug/protein interaction of at least twelve amino acids.

In a control experiment, taxol was added to purified GST from S. japonicum. In contrast to the Bcl-2/GST fusion construct, the GST spectra with and without taxol are virtually identical. The differences are far smaller than the error bars, and there is no change in the 220/210 nm ratio, nor is a peak shift observed. This means that were there any net structural change within the GST molecule alone, it would involve less than 0.5% of its total secondary structure. These results make it clear that taxol binding to the Bcl-2/GST fusion protein does occur, and the spectral differences observed for the Bcl-2/GST fusion protein must derive from the Bcl-2 portion of the molecule. Furthermore, this binding has significant structural consequences for the Bcl-2 protein, involving approximately 15% to 20% of the loop residues.

It has been shown that taxol or taxotere induces the phosphorylation of Bcl-2 and the apoptosis of 697 human acute leukemia pre-B cells (Haldar et al., 1995; 1997). The concentrations of these two drugs required to induce apoptosis in these cells is similar to the concentrations at which taxol and taxotere begin to interact with Bcl-2 in vitro. This suggests that it may be the direct interaction of these drugs with Bcl-2 that results in the observed phosphorylation and subsequent apoptosis. In addition, Human Bcl-2 differs significantly from the murine version of the protein in the region of the SEQ. ID NO. 3 motif. This difference may explain the poor response of mouse tumors to taxol therapies: currently, mouse models carrying human tissue tumors must be used in taxol studies.

The technique used here identifies Bcl-2 as a potential target for taxol and taxotere. The methods used are exceedingly simple. It is possible that members of the p3 library used in this work and containing the consensus SEQ. ID NO. 3 mimic the taxol binding site on Bcl-2 using the same amino acids that are present on Bcl-2.

EXAMPLE 2

Preparation of Biotinylated Taxol

The taxol derivatives, 7-biotinamidocarbamate 6 a-c, were synthesized as shown in Scheme I. Reaction of taxol and TESCl in pyridine at 0° C. gave 2'-TES-taxol 2 in 84% yield. Compound 2 reacted with carbonyldimidazole in CH$_2$Cl$_2$ at room temperature to yield the 2'-TES-7-imidazolidetaxol 3 in 94% yield. Treatment of 3 with a large excess of diamines H$_2$N(CH$_2$)$_n$NH$_2$ (50 equiv., n-4,6,12) in CH$_2$Cl$_2$ at room temperature afforded the aminocarbonates 4 (a, n-4; b, n=12). Without further purification, 4 a-c were treated with biotin N-hydroxylsuccinimide ester 7 at room temperature in DMF to give 2'-TES'7-biotinamidocarbamate 5a-c. Removal of the 2'-TES groups from 5a-c with HF/Py/MeCN (1:10:10 v/v/v) at room temperature afforded the desired 7-biotinamidocarbamated 6a-c after chromatography.

Scheme 1

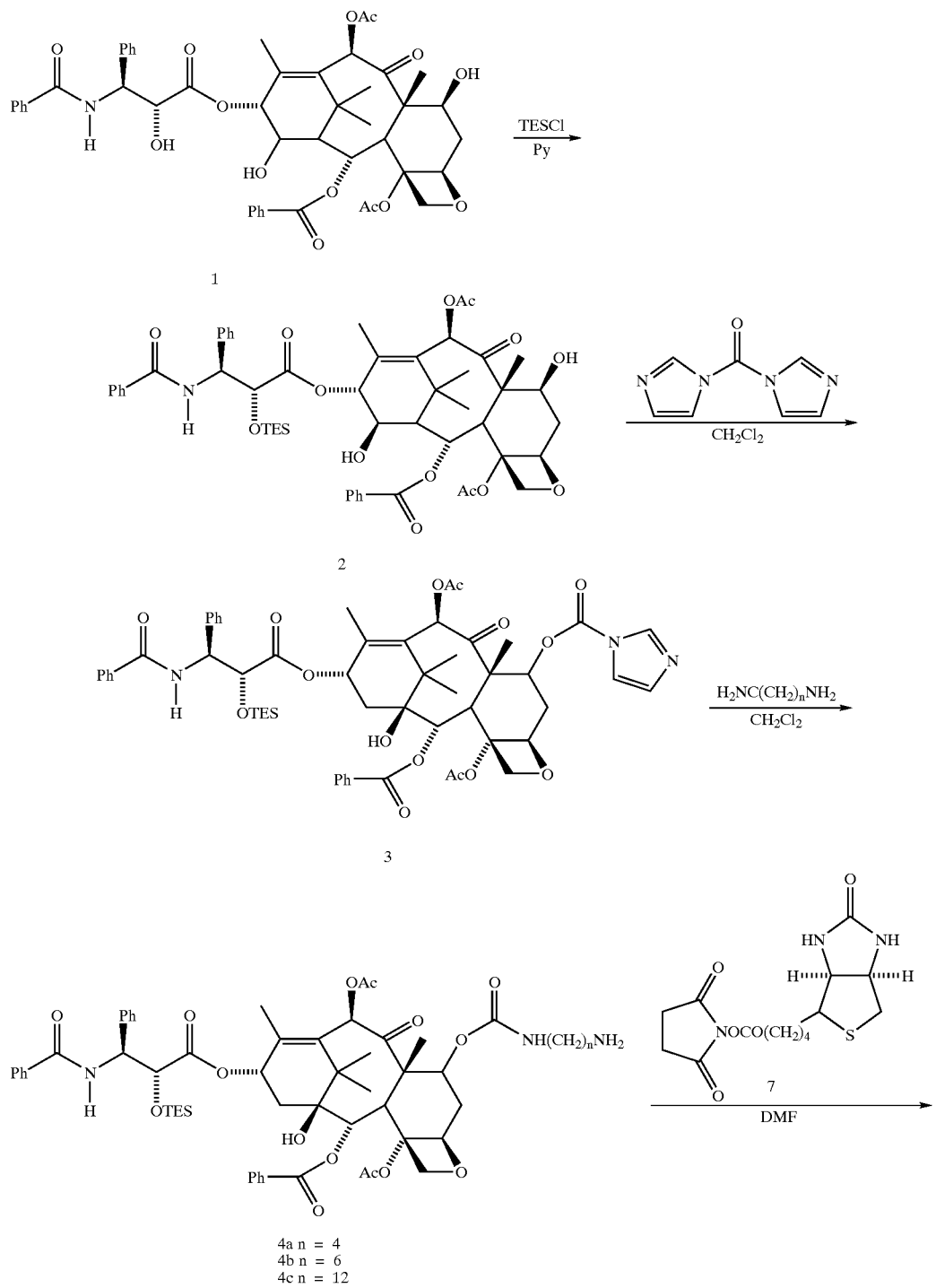

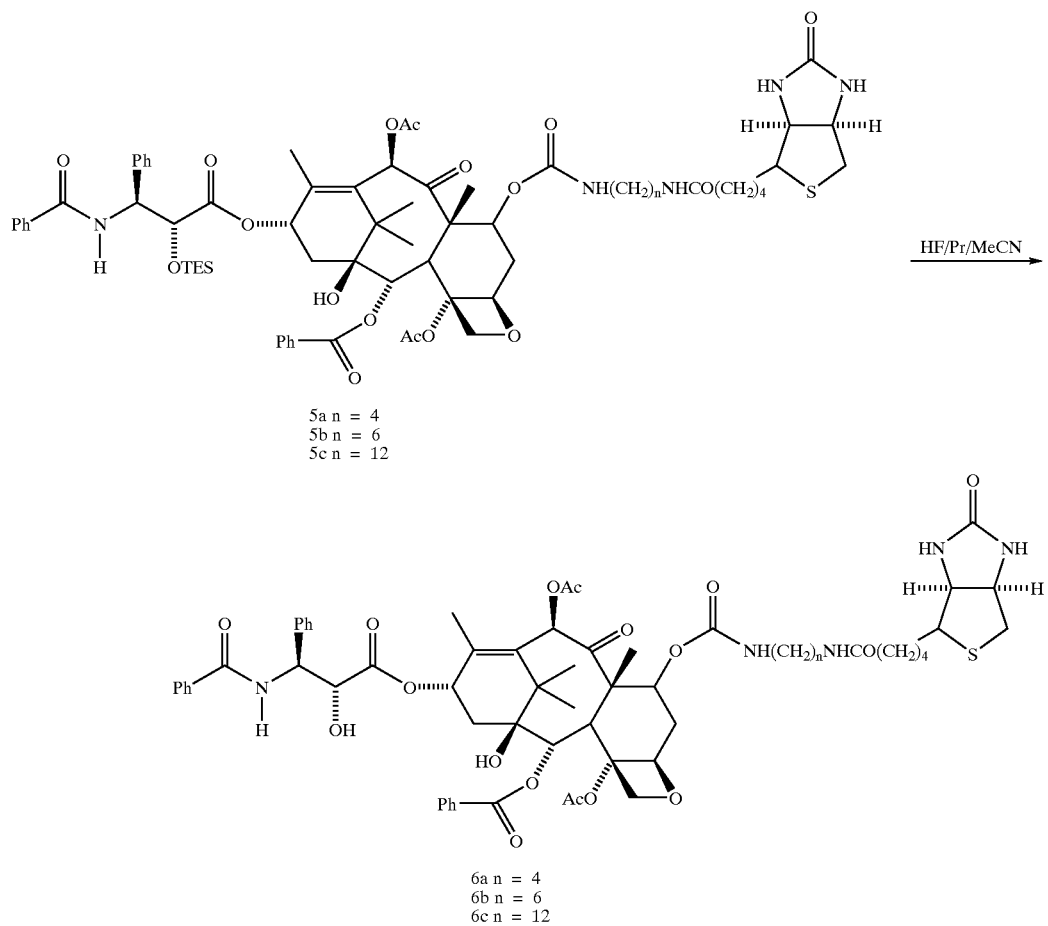

5a n = 4
5b n = 6
5c n = 12

6a n = 4
6b n = 6
6c n = 12

EXAMPLES

2'-TES-taxol 2. To a solution of taxol (247 mg, 0.289 mmol) in pyridine (2.9 mL) at 0° C. was added 0.87 mL of a 1.0 M solution of TESCI in pyridine (0.87 mmol). The mixture was stirred at 0° C. for 7 h, then at room temperature for 8 h, and diluted with EtOAc. The resulting mixture was washed with saturated aqueous $NaHCO_3$, water, 10% $CuSO_4$, water, and brine, dried over $Na_2SO_4$. The solvent was removed in vacuo to yield a light yellow oil (345 mg). Chromatography (3:2 v/v hexane/EtOAc) gave 2 as a white solid after removal of solvent (236 mg, 84%).

2'-TES-7-imidazolidetaxol 3. To a solution of 2'-TES-taxol (2, 251 mg, 0.259 mmol) in $CH_2Cl_2$ (10 mL) was added carbonyldiimidazole (422 mg, 2.60 mmol). The mixture was stirred at room temperature for 19 h, diluted with EtOAc (50 mL), washed with saturated aqueous $NaHCO_3$, water, brine, dried over $Na_2SO_4$. The solvent was removed in vacuo to yield 3 as a white solid (249 mg, 0.234 mmol, 91%).

Aminocarbonate 4a. To a solution of 3 (148 mg, 0.139 mmol) in $Ch_2Cl_2$ (10 mL) was added $H_2N(CH_2)_4NH_2$ (663 mg, 7.52 mmol). The mixture was stirred at room temperature for 16 h, diluted with EtOAc (50 mL), washed with saturated aqueous $NaHCO_3$, water, and brine, dried over $Na_2SO_4$. The solvent was removed in vacuo to yield 4a as a white solid (141 mg, 0.130 mmol, 94%).

Aminocarbonate 4b. To a solution of 3 (101 mg, 0.095 mmol) in $CH_2Cl_2$ (10 mL) was added $H_2N(CH_2)_6NH_2$ (558 mg, 4.80 mmol). The mixture was stirred at room temperature for 19 h, diluted with EtOAc (50 mL), washed with saturated aqueous $NaHCO_3$, water, and brine, dried over $Na_2SO_4$. The solvent was removed in vacuo to yield 4b as a white solid (99 mg, 0.089 mmol, 94%).

Aminocarbonate 4c. Compound 4c was similarly synthesized from 3 and $H_2N(CH_2)_{12}NH_2$ in good yield.

2'-TES-7-biotinamidocarbamate 5a. To a solution of 4a (141 mg, 0.130 mmol) in DMF (3 mL) was added biotin N-hydroxylsuccinimide ester (7, 50 mg, 0.15 mmol). The mixture was stirred at room temperature for 11 h, diluted with EtOAc (50 mL), washed with saturated aqueous $NaHCO_3$, water, and brine, dried over $Na_2SO_4$. The solvent was removed in vacuo and chromatography afforded as a white solid (132 mg, 0.101 mmol, 78%).

2'-TES-7-biotinamidocarbamate 5b. To a solution of 4a (99 mg, 0.089 mmol) in DMF (3 mL) was added biotin N-hydroxylsuccinimide ester (7, 36 mg, 0.11 mmol). The mixture was stirred at room temperature for 11 h, diluted with EtOAc (50 mL), washed with saturated aqueous $NaHCO_3$, water, and brine, dried over $Na_2SO_4$. The solvent was removed in vacuo to afford 5b as a white solid (117 mg, 0.088 mmol, 99%).

2'-TES-7-biotinamidocarbamate 5c. To a solution of 5c was similarly synthesized from 4c and 7 in good yield.

7-Biotinamidocarbamate 6a. A solution of a 5a (132 mg, 0.101 mmol) in 2 mL of HF/pyridine/MeCN (1:10:10 v/v/v) was stirred at room temperature for 30 min. diluted with EtOAc (50 mL), washed and saturated aqueous NaHCO$_3$, water, CuSO$_4$, water, and brine, dried over Na$_2$SO$_4$. Chromatography (1:5 v/v MeOH/CHCl$_3$) yielded 6a as a white solid (112 mg, 0.094 mmol, 93%). Anal. for C$_{62}$H$_{75}$N$_5$O$_{17}$S. (½)CHCl$_3$. Calcd. C:59.90;H:6.07. Found C:60.42; H:6.06.

7-Biotinamidocarbamate 6b. A solution of a 5b (117 mg, 0.088 mmol) in 2 mL of HF/pyridine/MeCN (1:10:10 v/v/v) was stirred at room temperature for 30 min. diluted with EtOAc (50 mL), washed and saturated aqueous NaHCO$_3$, water, CuSO$_4$, water, and brine, dried over Na$_2$SO$_4$. Chromatography (1:5 v/v MeOH/CHCl$_3$) yielded 6b as a white solid (97 mg, 0.079 mmol, 90%). Anal. for C$_{64}$H$_{79}$N$_5$O$_{17}$S.3H$_2$). Calcd. C:60.22;H:6.66. Found C:60.47; H:6.68.

7-Biotinamidocarbamate 6c. Similar reaction and workup from 5 c gaive 6 c as a white solid (110 mg). Anal. for C$_{70}$H$_{91}$N$_5$O$_{17}$S.(½)SHCl$_3$. Calcd. C:61.98; H: 6.75. Found C:61.77; H: 6.98.

EXAMPLE 3

Identification of Dioxin-Binding Peptides

Dioxin is a pervasive environmental toxin that exhibits toxic effects at very low doses. For the most part, toxicologists believe that its effect is due to the interaction of dioxin with a single molecular target, the aryl hydrocarbon receptor (AhR) (Birnbaum, 1994). However, the effects of dioxin are so pleiotropic that the possibility of other molecular targets cannot be ruled out. Dr. Valery Petrenko (U. Missouri, Columbia) screened a random peptide library for affinity to a biotinylated dioxin (Petrenko et al., 1996). A single tetrapeptide consensus sequence, EPFP (SEQ. ID NO. 5), was obtained from this screening of a random peptide library fused to the p8 coat protein of the M13 phage. p8 libraries are significantly different from p3 libraries used by the applicants in example 1 in that there are ~3000 copies of p8 on a virion, and only 5 p3 proteins. Therefore, the avidity of the interaction becomes more important and weaker interactions may lead to binding of phage to the target. Another weakness of the p8 libraries is that the fact that there are so many inserts per virion that the synthesis of the inserts produces an observable effect on the host metabolism (Rodi et al. (1997) *Proceedings of the 22nd Tanaguchi International Symposium.* (Nov. 18–21, 1996)). Because of this, there is very significant censorship of the library due to a broad set of selection factors ranging from protein synthesis to virion assembly. It has been demonstrated that certain sequences are highly favored in p8 libraries, particularly sequences containing proline (P) and phenylalanine (F) (Cesareni, et al., 1997). Consequently, it is difficult to know if the putative dioxin binding motif observed by Petrenko is a dioxin binding motif, or simply a consequence of the growth needs of his library. These data illustrate the need to consider growth and selection factors when choosing a peptide library. Nevertheless, Petrenko demonstrated that the EPFP (SEQ. ID NO. 5) motif does indeed bind to dioxin when displayed on p8.

The applicants searched the peptide data banks for proteins containing SEQ. ID NO. 5. Since the size of the random peptides in the library was relatively small (8 amino acids), and the derived consensus was only 4 amino acids in length, there were a large number of human and mammalian proteins in which it is found. After searching the literature, the applicants determined that one of them, Leukemia Inhibitory Factor, when overexpressed in mice, resulted in some toxic effects similar to those observed at very high doses of dioxin (Hilton et al., 1991). Having made this correlation, the applicants determined that affinity of dioxin for LIF would be the first of the proteins containing the putative dioxin binding motif that would be tested for binding to biotinylated dioxin.

ELISA experiments have demonstrated that biotinylated dioxin does indeed bind to LIF. The applicants utilized the same biotinylated dioxin as Petrenko in an ELISA assay for binding to LIF, to several mutants of the LIF protein changed in the EPFP homology domain (residues 50–53), to anti-dioxin antibodies as a positive control, and to ciliary neurotrophic factor (CNTF) (structurally similar to LIF but lacking the SEQ. ID NO. 5 motif) as a negative control. Results of these experiments are shown in FIG. 4. LIF binds to human and murine LIF with a K$_D$ of approximately 10–100 µM, indicating an affinity approximately 10,000 fold less than the anti-dioxin antibodies used as a positive control. The negative control CNTF exhibited no binding to LIF. When several point mutations of LIF were tested, it was found that binding was reduced in a Pro-53-Ala mutant to undetectable levels; a Phe-156-Ala mutant exhibited a reduction of about three-fold in binding (in the three dimensional structure of LIF Phe 156 is adjacent to the EPFP (SEQ. ID NO. 5) dioxin binding motif; and a Pro-51-Ala mutant showed no change in binding. These results indicate that (i) dioxin binds to LIF at detectable affinities and at affinities greater than other proteins that are similar in sequence and structure but lack the EPFP motif; (ii) alteration of the EPFP motif may lead to a decrease in the observed dioxin levels; and (iii) other residues in the immediate vicinity of the EPFP motif (i.e. Phe 156) also are involved in dioxin binding.

Correlation of the putative binding site for dioxin with the residues known to be involved in the binding of LIF to the LIF-receptor (LIFR), indicates that dioxin binds directly to a control region that modulates the LIF-LIFR interaction (Robinson et al., 1994). Enhancement of the LIF-LIFR interaction may lead to wasting and potentially to endometriosis; toxic effects implicated in dioxin exposure and in LIF overexpression.

Petrenko (Petrenko et al., 1996) demonstrated that the peptide consensus sequence EPFP (glu-pro-phe-pro) displayed affinity for biotinylated dioxin. He did not, however, bring the result any further. The applicants followed up on this result by screening GenBank for proteins containing EPFP and discovered that the aryl hydrocarbon receptor (AhR), known to bind dioxin, has a motif with a similar sequence. The applicants have further shown that the sequence EPFP allows the identification of leukemia inhibitory factor (LIF) as a potential target of dioxin, and have now demonstrated that dioxin does indeed bind to LIF with at least micromolar affinity.

The applicants have also duplicated Petrenko's binding experiment with p3-M13 phage coat protein expression system using a random 12 amino acid peptide library (Ph.D-12) In a p3 system, approximately 3–5 peptides are displayed per phage, as per example 1. Because the peptide motifs were being presented in different conformational scaffolds (12 versus 8 amino acids), at a much higher affinity stringency (3 versus 3000 copies of the peptide per phage), and under conditions which were non-competitive, the applicants did not necessarily expect to obtain the same consensus data as Petrenko. In fact, applicants did not see the same EPFP (SEQ. ID NO. 5) consensus sequence emerge.

Rather, the applicants did see a particular statistical trend towards the selection against glutamic acid and for serine residues amongst peptides with improved dioxin binding. The results are show in the following table. Column A contains data on amino acid frequencies from 101 peptides selected at random from the peptide library; column B, frequencies from 69 peptides selected for binding to taxol (2 rounds of selection); column C, frequencies from 89 peptides selected for binding to dioxin (2 and 3 selection rounds data merged). The frequencies for all these amino acids are very similar reflecting the fact that many (70–80%) of the peptides isolated after selection for binding are, in fact, due to non-specific binding.

TABLE 1

| amino acid | unselected | taxol selected | dioxin selected |
|---|---|---|---|
| A | 7.398 | 7.824 | 7.397 |
| C | 0.914 | 0 | 0 |
| D | 3.491 | 2.812 | 2.622 |
| E | 2.909 | 2.812 | 1.498 |
| F | 2.993 | 2.445 | 2.809 |
| G | 2.993 | 2.689 | 3.371 |
| H | 5.653 | 6.724 | 5.337 |
| I | 3.159 | 3.423 | 3.933 |
| K | 3.076 | 2.200 | 2.528 |
| L | 10.058 | 7.457 | 9.457 |
| M | 3.159 | 3.301 | 2.715 |
| N | 4.738 | 4.279 | 4.775 |
| P | 10.723 | 12.347 | 11.423 |
| Q | 4.489 | 4.401 | 5.431 |
| R | 5.071 | 5.134 | 4.963 |
| S | 8.645 | 12.469 | 11.423 |
| T | 9.975 | 9.902 | 10.300 |
| V | 4.655 | 5.012 | 4.869 |
| W | 2.244 | 1.589 | 2.154 |
| Y | 3.658 | 3.178 | 2.996 |

From these data, it can be seen that significant additional information about the preference of certain peptides for dioxin has been gathered, considering that the data are as statistically significant as that obtained for taxol. However, this example also illustrates that the use of different peptide libraries and genetic packages may lead to different information of varying usefulness to a particular investigation, and that several different libraries and genetic packages preferably will be tried to obtain the best results for a particular application of the method.

In light of the detailed description of the invention and the examples presented above, it can be appreciated that the several objects of the invention are achieved. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

REFERENCES

Birnbaum, L. S. The mechanism of dioxin toxicity: Relationship to risk assessment. Environmental Health Perspectives, 102 (suppl. 9) 157–167 (1994).
Bogdan, C. and Ding, A., Taxol, a microtubule-stabilizing, anti-neoplastic agent induces expression of tumor necrosis factor a and interleukin 1 in macrophages. *J. Leukocyte Biol.* 52; 119–122 (1992).
Cesareni, G, et al., 1997: "Construction, exploitation and evolution of a new peptide library displayed at high density by fusion to the major coat protein of filamentous phage," *Biol. Chem.* 378:517–521.
Chang, B. S., Minn, A. J., Muchmore, S. W., Fesik, S. W. and Thompson, C. B. Identification of a novel regulatory domain in Bc-$x_L$ and Bcl-2. *EMBO Journal* (in press).
Dayhoff, M. O., et al., *Atlas of protein sequence and structure,* 3:33.
Fields, B. A., Goldbaum, F. A., Ysern, X., Poljak, R. J. & Mariuzza, R. A. Molecular basis of antigen mimicry by an anti-idiotope Nature 374, 739–742 (1995).
Gies, J.-P. Drug targets—Molecular mechanisms of drug action. in *The Practice of Medicinal Chemistry* (Academic Press, London; ed. Wermuth, C. G.) pp. 55–80.
Haldar, S., Jena, N and Croce, C. M., Inactiviation of bcl-2 by phosphorylation. *Proc. Natl. Acad. Sci. USA* 92, 4507–4511 (1995).
Haldar, S., Chintapalli, J. and Croce, C. M., Taxol-induced bcl-2 phosphorylation and death of prostate cancer cells. *Cancer Res.* 56, 1253–1255 (1996).
Haldar, S., Basu, A. and Croce, C. M. Bcl2 is the guardian of microtubule integrity. *Cancer Research.* 57, 229–233 (1997).
Henikoff, S., et al., 1992: "Amino acid substitution matrices from protein blocks" PNAS 89:10915–10919.
Hilton, D. J., Nicola, N. A., Waring, P. M. and Metcalf, D. Clearance and fate of leukemia inhibitory factor (LIF) after injection into mice. J. Cell. Physiol. 148; 430–439 (1991).
Hoffman, N. G., Sparks, A. B., Carter, J. M. and Kay, B. K. Binding properties of SH3 peptide ligands identified from phage-displayed random peptide libraries. *Molecular Diversity* 2, 5–12 (1996).
Jordan, M. A., Toso, R. J., Thrower, D., Wilson, L. Mechanism of mitotic block and inhibition of cell proliferation by taxol at low concentrations. *Proc. Natl. Acad. Sci. USA* 90, 9552–9556 (1993).
Kay, B. K., Winter, J. and McCafferty, J. (eds.) Phage display of peptides and proteins. A laboratory manual. Academic Press (1996).
Minor, D. L. and Kim, P. S. Context-dependent secondary structure formation of a designed protein sequence Nature 380 730–734 (1996).
Muchmore, S. W., Sattler, M., Liang, H., Meadows, R. P., Harlan, J. E., Yoon, H. S., Nettesheim, D., Chang, B. S., Thompson, C. B., Wong, S.-L., Ng, S.-C., and Fesik, S. W. X-ray and NMR structure of human, an inhibitor of programmed cell death. *Nature,* 381, 335–341 (1996).
Ohdo, S., Ogawa, N., Song, J. G. Chronopharmacological study of acetylsalicylic acid in mice. *Eur. J. Pharmacol.,* 293: 151–57 (1995).
Petrenko, V. A., Smith, G. P., Gong, X., and T. Quinn A library of organic landscapes on filamentous phage. Protein Engineering 9, 797–801 (1996).
Robinson, R. C., Grey, M. L., Staunton, D., Vankelecom, H., Vernallis, A. B., Moreau, J.-F., Stuart, D. I., Heath, J. K. and jones, E. Y. The crystal structure and biological function of leukemia inhibitory factor: Implications for receptor binding. Cell 77, 1101–1116 (1994).
Rodi, D. J. and L. Makowski (1997) Transfer RNA isoacceptor availability contributes to sequence censorship in a library of phage displayed peptides. in *Proceedings of the 22nd Tanaguchi International Symposium.* (Nov. 18–21, 1996).
Roth, W., et al. (1998) *British J. Cancer* 77:404–411.
Rowinsky, E. K. and Donehower, R. C. Taxol: twenty years later, the story unfolds. *J. Natl. Cancer Inst.* 83, 1778–1781 (1991).
Scott, J. K. & Smith, G. P. Searching for peptide ligands with an epitope library. Science, 249; 386–390.
Sparks, A. B., Rider, J. E., Hoffman, N. G., Fowlkes, D. A., Quilliam, L. A. and Kay, B. K. Distinct ligand preferences of Src homology domains from Src, Yes, Abl, Cortactin, p53 bp2, PLCγ, Crk and Grb2 *Proc. Natl. Acad. Sci.* 93; 1540–1544 (1996b).

Sparks, A. B., Hoffman, N. G., McConnell, S. J. Fowlkes, D. A. and Kay, B. K. Cloning of ligand targets: Systematic isolation of SH3 domain containing proteins. *Nature Biotechnology* 14; 741–744 (1996a).

van Regenmortel, M. H. V., The recognition of proteins and peptides by antibodies. in *Immunochemistry.* 277–300, (van Oss, C. J. and van Regenmortel, M. H. V., eds.), Marcel Dekker, Inc.; New York (1994).

Wilson, I. A., Haft, D. H., Getzoff, E. D., Tainer, J. A., Lerner, R. A., & Brenner, S. B. Identical short peptide sequences in unrelated proteins can have different conformations: A testing ground for theories of immune recognition. Proc. Natl. Acad. Sci. USA, 82, 5255–5259 (1985).

Yin, C., Knudson, C. M., Korsmeyer, S. J. and Van Dyke, T. Bax suppresses tumorigenesis and stimulates apoptosis. *Nature* 385, 637–640 (1997).

We claim:

1. A process for the identification of a protein which binds to a ligand, wherein the ligand is an organic molecule conjugated with a plating agent, the ligand having a molecular weight which is less than 5.000 Daltons and being other than a nucleic acid, peptide or protein, the process comprising:

screening the ligand against a peptide or protein library wherein the peptide or protein members of the library are selected from the group consisting of expression products of a cDNA library derived from a cell and fragments of those expression products, and wherein the library comprises genetic packages which physically link each peptide or protein member of the library to a nucleic acid polymer which encodes that member, separating form the library members of the library which have an affinity for the ligand which is greater than the affinity possessed by other members of the library for the ligand, determining the nucleic acid sequence which encode the members which have been separated from the library and translating these nucleic acid sequences into peptide sequences, and identifying, protein(s) which contain a portion of the translated peptide sequences or which correspond to consensus peptide sequences derived from statistical analysis of said translated library member peptide sequences.

2. A process for the identification of a protein which binds to a ligand, the ligand having a molecular weight which is less than 5.000 Daltons and being other than a nucleic acid, peptide or protein, the process comprising:

screening the ligand against a peptide or protein library wherein the peptide or protein members of the library are selected from the group consisting of expression products of a cDNA library derived from a cell and fragments of those expression products, and wherein the library comprises genetic packages which physically link each peptide or protein member of the library to a nucleic acid polymer which encodes that member, separating from the library members of the library which have an affinity for the ligand which is greater than the affinity possessed by other members of the library for the ligand, determining the nucleic acid sequences which encode the members which have been separated from the library and translating these nucleic acrid sequences into peptide sequences, and identifying protein(s) which contain a portion of the translated peptide sequences, or which correspond to consensus peptide sequence derived from statistical analysis of said translated library member peptide sequences.

3. The process of claim 2 wherein the peptide or protein members of the library comprise an equal distribution of possible peptide sequences.

4. A process for the identification of a protein which binds to a ligand, wherein the ligand is an organic molecule conjugated with a plating agent, the ligand having a molecular weight which is less than 5,000 Daltons and being other than a nucleic acid, peptide or protein, the process comprising:

screening the ligand against a peptide or protein library, wherein the peptide or protein members of the library comprise an equal distribution of possible peptide sequences, aid wherein the library comprises genetic packages which physically link each peptide or protein member of the library to a nucleic acid polymer which encodes that member, separating from the library members of the library which have an affinity for the ligand which is greater than the affinity possessed by other members of the library for the ligand, determining the nucleic acid sequences which encode the members which have been separated from the library and translating these nucleic acid sequences into peptide sequences, and identifying protein(s) which contain a portion of the translated peptide sequences or which correspond to consensus peptide sequences derived from statistical analysis of said translated library member peptide sequences.

5. A process for the identification of a protein which binds to a ligand the ligand having a molecular weight which is less than 5,000 Daltons and being other than a nucleic acid, peptide or protein, the process comprising:

screening the ligand against a peptide or protein library, wherein the peptide or protein members of the library comprise an equal distribution of possible peptide sequences, and wherein the library comprises genetic packages which physically link each peptide or protein member of the library to a nucleic acid polymer which encodes that member, separating from the library members of the library which have an affinity for the ligand which is greater than the affinity possessed by other members of the library for the ligand, determining the nucleic acid sequence which encode the members which have been separated from the library and translating these nucleic acid sequences into peptide sequences, and identifying protein(s) which contain a portion of the translated peptide sequences ox which correspond to consensus peptide sequences derived from statistical analysis of said translated library member peptide sequences.

6. A process for the identification of a protein which binds to a ligand, the ligand having a molecular weight which is less than 5,000 Daltons and being other than a nucleic acid peptide or protein the process comprising:

screening the ligand Sand against a peptide or protein library, wherein the library comprises genetic packages which physically link each peptide or protein member of the library to a nucleic acid polymer which encodes that member, separating firm the library members of the library which have an affinity for the ligand from members of the library with lower affinity for the ligand by alternating a differentiation method selected from the group consisting of biopanning, chromatography, Western or Southern blotting, and electrophoresis with amplification of the genetic packages containing those members of the library with greater affinity for the ligand, determining the nucleic acid sequences which encode the members which have been separated from the library and translating these nucleic acid sequences into peptide sequences, and identifying protein(s) which contain a portion of the translated peptide sequence, or which correspond to consensus peptide sequences derived from statistical analysis of said translated library member peptide sequences.

7. The method of claim 6 wherein the separation is effected by about two to three rounds of alternating the differentiation method and amplification of the genetic package.

\* \* \* \* \*